US008295432B2

(12) United States Patent
Spartiotis et al.

(10) Patent No.: US 8,295,432 B2
(45) Date of Patent: Oct. 23, 2012

(54) RADIATION IMAGING DEVICE WITH IRREGULAR RECTANGULAR SHAPE AND EXTRAORAL DENTAL IMAGING SYSTEM THEREFROM

(75) Inventors: Konstantinos Spartiotis, Espoo (FI); Tom Schulman, Porvoo (FI); Tuomas Pantsar, Espoo (FI)

(73) Assignee: Oy AJAT Ltd, Espoo (FI)

( * ) Notice: Subject to any disclaimer, the term of this patent is extended or adjusted under 35 U.S.C. 154(b) by 358 days.

(21) Appl. No.: 12/772,251

(22) Filed: May 3, 2010

(65) Prior Publication Data

US 2010/0208866 A1 Aug. 19, 2010

Related U.S. Application Data

(60) Continuation-in-part of application No. 11/819,018, filed on Jun. 25, 2007, now Pat. No. 7,742,560, which is a continuation-in-part of application No. 11/673,583, filed on Feb. 11, 2007, now Pat. No. 7,676,022, which is a division of application No. 11/277,530, filed on Mar. 27, 2006, now Pat. No. 7,336,763.

(60) Provisional application No. 60/677,020, filed on May 2, 2005.

(51) Int. Cl.
*A61B 6/14* (2006.01)
*H01L 24/146* (2006.01)
(52) U.S. Cl. .................. 378/38; 378/22; 378/39
(58) Field of Classification Search .......... 378/22, 378/38, 39, 54, 62, 98.8; 250/370.09, 370.13
See application file for complete search history.

(56) References Cited

U.S. PATENT DOCUMENTS

| | | | |
|---|---|---|---|
| 4,188,537 | A | 2/1980 | Franke |
| 4,823,369 | A | 4/1989 | Guenther et al. |
| 4,878,234 | A | 10/1989 | Pfeiffer et al. |
| 4,995,062 | A | 2/1991 | Schulze-Ganzlin et al. |
| 5,195,114 | A | 3/1993 | Sairenji et al. |
| 5,383,097 | A | 1/1995 | Delucia et al. |
| 5,784,429 | A | 7/1998 | Arai |
| 6,049,584 | A | 4/2000 | Pfeiffer |
| 6,118,842 | A | 9/2000 | Arai et al. |
| 6,448,544 | B1 | 9/2002 | Stanton et al. |
| 6,466,641 | B1 | 10/2002 | Virta et al. |
| 6,496,557 | B2 | 12/2002 | Wilson et al. |
| 7,016,461 | B2 | 3/2006 | Rotondo et al. |
| 7,136,452 | B2 | 11/2006 | Spartiotis et al. |
| 7,340,032 | B2 | 3/2008 | Besson |

(Continued)

FOREIGN PATENT DOCUMENTS

EP 0 138 647 A2 4/1985

(Continued)

OTHER PUBLICATIONS

PCT International Search Report mailed Feb. 1, 2010, in PCT Application.

(Continued)

*Primary Examiner* — Anastasia Midkiff
(74) *Attorney, Agent, or Firm* — Young & Thompson

(57) ABSTRACT

A radiation imaging device includes plural individual detectors defining an irregular rectangular active area responsive to x-rays and with different widths along a length of the active area. The individual detectors may be of different rectangular shapes and mounted on a motherboard. The motherboard may be formed of a first module mounting a first of two individual detectors and a second module detachable connected to the first module and mounting a second of two individual detectors.

20 Claims, 6 Drawing Sheets

U.S. PATENT DOCUMENTS

| | | |
|---|---|---|
| 7,426,260 B2 | 9/2008 | Cantu et al. |
| 7,515,678 B2 | 4/2009 | Hsieh et al. |
| 2001/0048732 A1 | 12/2001 | Wilson et al. |
| 2004/0133095 A1 | 7/2004 | Dunki-Jacobs et al. |
| 2004/0190678 A1 | 9/2004 | Rotondo et al. |
| 2005/0249331 A1 | 11/2005 | Wear et al. |
| 2006/0011852 A1 | 1/2006 | El-Hanany et al. |
| 2006/0126781 A1 | 6/2006 | Hartung et al. |
| 2006/0233301 A1 | 10/2006 | Erhardt et al. |

FOREIGN PATENT DOCUMENTS

| | | |
|---|---|---|
| EP | 0 421 869 A1 | 4/1991 |
| EP | 0 673 623 A1 | 9/1995 |
| GB | 2 228 765 A | 12/1994 |
| JP | 07-275240 | 10/1995 |
| JP | 09-122118 | 5/1997 |
| JP | 10-225455 | 8/1998 |
| JP | 2002-017718 | 1/2002 |
| WO | 02/052505 A2 | 7/2002 |
| WO | 03/077319 A2 | 9/2003 |
| WO | 2004/055550 A1 | 7/2004 |
| WO | 2006/109806 | 12/2006 |
| WO | 2004/084728 A | 10/2007 |

OTHER PUBLICATIONS

Certified Translation of PCT/DE04/00620.

RADIATION IMAGING DEVICE WITH IRREGULAR RECTANGULAR SHAPE AND EXTRAORAL DENTAL IMAGING SYSTEM THEREFROM

CROSS REFERENCE TO RELATED APPLICATIONS

The present application is a continuation-in-part of prior filed U.S. patent application Ser. No. 11/819,018 which claimed the benefit of prior filed U.S. patent application Ser. No. 11/673,583 filed 11 Feb. 2007 which claimed the benefit of prior filed U.S. patent application Ser. No. 11/277,530 filed 27 Mar. 2006, which claimed the benefit of prior filed U.S. Provisional Application Ser. No. 60/677,020 filed 2 May 2005, which are all incorporated herein by reference, and to which the present application is a continuation-in-part US national non-provisional utility patent application.

BACKGROUND OF THE INVENTION

1. Field of the Invention

The present invention relates to digital radiation imaging. In particular, the invention relates to the effective construction of optimized imaging areas of various size and shape by combining separate semiconductor pixel detectors side by side in a mosaic like manner so that the shape of the active area of the sensor is made to match as exactly as possible the X-ray beam shape (or shapes) of a specific application.

2. Description of Related Art

A major problem in constructing digital X-ray imaging devices is the manufacturing of large sensor areas. Commercial state of the art large area devices generally rely on flat panel technology. Sensors based on other technologies such as scintillator-CCD sensors or especially semiconductor-CMOS sensors produce higher image quality but suffer from a more limited active imaging area possible to manufacture.

The maximum continuous active area of single detector chip CCD and CMOS based sensors is typically a few square centimeters ($cm^2$). These single detector chips may be combined by mounting them side by side in a mosaic like manner to form larger areas. Such mosaic constructions have been successfully applied in scanning systems in which the active imaging area has a slot shape to form a linear array of imaging elements. Rectangular shape imaging areas of a few tens of $cm^2$ have also been successfully manufactured. Larger rectangular areas of CCD and CMOS based sensors are limited by the fact that one side of the single CCD and CMOS chips is always required for external electrical connections and prevents side by side mounting at that one side. Benefits of constructing imaging areas from separate small detector elements include flexibility to form areas of irregular shape and cost effective production. Prior art sensors, however, have not been able to address these needs.

Some applications may demand different sensor areas for different imaging modes. For example in modern digital dental extraoral X-ray imaging the same imaging system should be able to perform both fan beam panoramic scan acquisition and cone beam three dimensional (3D) imaging. In the scan mode a vertical relatively long slot like imaging area is preferred in order to match the sensor area with the X-ray fan beam shape and to optimize readout speed. In the 3D mode a vertically shorter but horizontally wider sensor area is optimal in providing appropriate cone beam coverage.

In the prior art, to match these partially contradicting sensor area requirements manufacturers of modern dental extraoral X-ray systems either have to use two separate available state of the art digital sensors or one large sensor (typically flat panel) with a sufficient area of rectangular shape to cover both the fan and the cone beam shapes. Both of these options introduce disadvantages in terms of cost, compactness and effective use. The present invention deals with this issue by introducing a novel digital X-ray sensor with a unique irregular shape of active area optimized for both of the imaging modes mentioned above. Dental extraoral X-ray imaging is here given as an example only. The invention can be used for benefit in any other X-ray imaging application with similar requirements of imaging area. The invention can be realized especially well with semiconductor-CMOS detector technology but may also be realized with other technologies such as the scintillator-CCD technology.

Several ideas and methods of constructing larger mosaic type active imaging areas of single detector elements have been introduced and patented [U.S. Pat. No. 6,207,744, U.S. Pat. No. 5,812,191, EP0421869, WO9708751, EP0138647]. The aim of such methods is generally to realize a large enough regular imaging area of either rectangular or slot shape. Most of the presented methods teach techniques to minimize the unavoidable dead space or blind region between the separate detector elements. The minimum gap between the active areas of adjacent detector elements is obviously achieved by mounting the elements in physical contact with each other. While eliminating or minimizing the inter-element dead space of multi element sensors is the ideal for acquiring uniform X-ray images it may not be feasible from the manufacturing point of view to assemble the separate detector elements physically touching each other. In addition to the optimal irregular shape of active area mentioned above the present invention introduces an effective manufacturing technique for multi element sensors. This technique is especially applicable to sensors based on semiconductor-CMOS technology and has specific relevance to CdTe-CMOS pixel detectors.

SUMMARY OF THE INVENTION

The present invention provides an X-ray imaging sensor with a unique irregular shape of active area differing from a rectangular shape, the shape being optimized to the requirements of the application of the sensor. As illustrated in FIG. 1, the shape of the active area of the sensor may be wider at one end 16 and narrower at the other end 17. Alternatively, the sensor may be narrow at both ends of the active area and wider in the center 18 or vice versa. The shape may be symmetric or asymmetric in relation to the center lines of the active area. The active area of the sensor is, as shown in FIG. 1, preferably constructed of separate detector elements 1 in a mosaic like manner. The shape of the active area can, therefore, be almost any combination of small rectangles of various sizes. The shape may even include discontinuities or open space 2 in the middle of the active area depending on the requirements of the application.

An important aspect of the invention is that the shape of the active area of the sensor is made to match as exactly as possible the X-ray beam shape (or shapes) of a specific application. If the X-ray beam shape differs significantly from a cone or a fan beam shape or if the application requires the use of two or more X-ray beams with different shapes no conventional sensor of linear or rectangular shape will match effectively the X-ray beam shapes. For example, in an application using a fan beam and a rectangular cone beam for different imaging modes a sensor with irregular shape of active area provides much more efficient beam coverage than a conventional sensor with a large rectangular active area. The benefits of an optimized sensor area include savings in material costs, faster data readout and the possibility to use one sensor instead of many for different beam shapes.

Another aspect of the invention is the method of manufacturing the mosaic like sensor structure by leaving a finite physical gap between adjacent detector elements. This structure is a departure from the prior art teachings of eliminating dead space between individual detector chips. This inventive manufacturing method of not providing minimum dead space within the active imaging area brings definite advantages in terms of production yield and long term endurance of the sensor. Since solid state semiconductors are generally fragile crystals, mounting them in physical contact increases greatly the risk of damaging the crystal edges with cracks or fractures during production. It also leaves the detector elements much more vulnerable to damage caused by thermal expansion or mechanical shock compared to the method of mounting the elements with an intermediate physical gap. Moreover, physical contact between the semiconductor detector crystals can lead to distortions in the signal collecting electric field applied to the crystals. The gap between the detector elements may be simply empty space or the gap may be created by placing some material such a mylar film in between the detector elements. The size of the gap is preferably but not necessary equal to or a multiple of the pixel size of the detector elements.

Still another aspect of the invention is the effective method of manufacturing several different mosaic type sensors with active areas of dissimilar irregular shape on identical sensor substrates the substrate being generally a printed circuit board (PCB). Since the control and signal readout schemes of the separate detector elements are identical it is possible to design one PCB to accommodate different combinations of detector elements. Thus with one type of a PCB and one (or more) type of a detector element, sensors with various shapes of active area for different applications can be produced easily and without the need of any costly and time consuming design changes of the substrate. Alternatively, a desired shape of the active sensor area can be constructed by combining side by side two or more separate either identical or non-identical sensor substrates each substrate populated with one or more detector elements of either similar or dissimilar size or shape.

The invention especially applies to X-ray imaging sensors made of CdTe-CMOS pixel detectors but it is not limited to this technology and also finds relevance in other technologies as well such as in the scintillator-CCD technology.

The invention is to be used in particular in dental extraoral X-ray imaging but is beneficial in other application as well.

DESCRIPTION OF PREFERRED EMBODIMENTS

A inventive radiation imaging device includes plural individual detectors defining an irregular rectangular active area responsive to x-rays and with different widths along a length of the active area. The individual detectors may be of different rectangular shapes and mounted on a motherboard. The motherboard may be formed of a first module mounting a first of two individual detectors and a second module detachable connected to the first module and mounting a second of two individual detectors.

Figure 2:
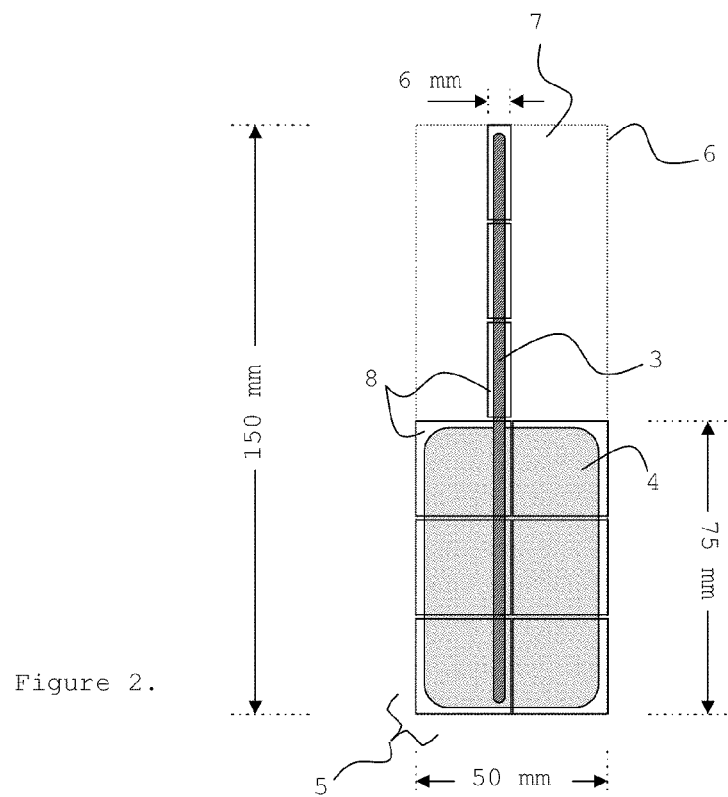
FIG. 2 illustrates a preferred shape of the active area of the invented X-ray sensor designed for dental extraoral X-ray imaging.

A preferred shape 5 of the active area of the invented X-ray sensor is shown in FIG. 2. The shape 5 is in this example constructed from nine individual detector elements 8 and is designed for the needs of modern dental extraoral X-ray imaging in which a fan beam 3 is, at the same time, used for panoramic scan imaging and a rectangular cone beam 4 is used for 3D tomographic imaging. Typical dimensions of the preferred active area are given in FIG. 2. As can be observed from FIG. 2, the beam coverage of the preferred active sensor area 5 of irregular shape is much better than that of a large conventional rectangular area 6. The rectangular shape 6 leaves much more useless sensor area 7 both in the panoramic mode (fan beam) and in the 3D mode (cone beam).

Figure 1:
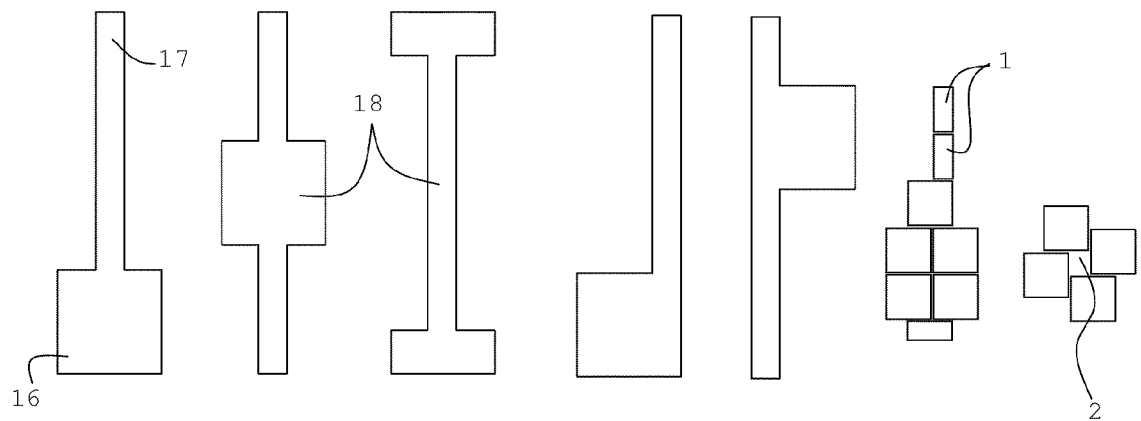
FIG. 1 illustrates various options of irregular shape of the active area of the invented X-ray sensor.

As illustrated by FIGS. 1-2, in each case the inventive radiation imaging device includes an active area responsive to x-rays. The active area has an irregular rectangular shape with an overall length y (150 mm in FIG. 2) and an overall width x (50 mm in FIG. 2). Advantageously, each imaging device has different local widths (50 mm, 6 mm in FIG. 2) for corresponding different ranges along the length (respectively the lower and upper halves of the FIG. 2 device).

Figure 3:
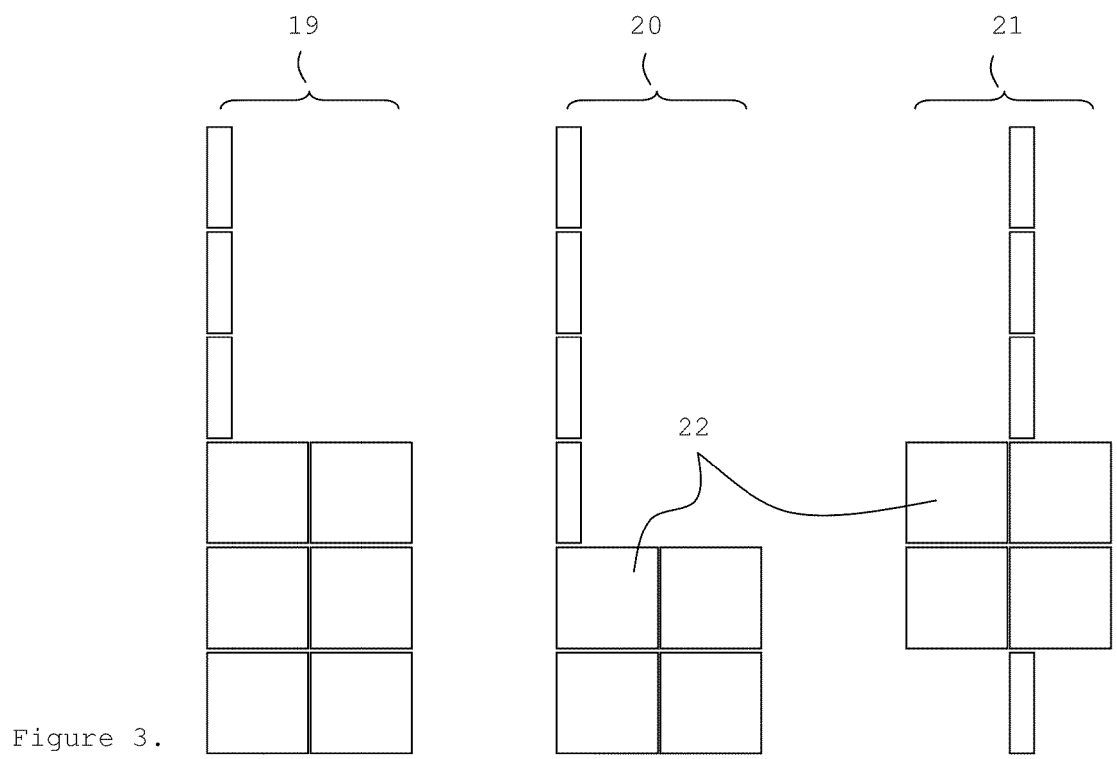
FIG. 3 illustrates preferred shapes of the active area of the invented X-ray sensor designed for dental extraoral X-ray imaging.

FIG. 3 shows three other preferred shapes 19, and 21 of active sensor area in the application of dental extraoral X-ray imaging. Many other similar shapes can also be used in dental extraoral imaging. The choice of shape depends on the X-ray beam shapes of the application. The shape 19 provides coverage for a larger cone beam which may be desired to acquire image data from a larger area for more comprehensive 3D or transverse slicing (tomographic) imaging. The shapes 20 and 21 provide less cone beam coverage resulting in a more economic sensor solution. In shape 21 the cone beam area 22 is lifted higher up than in shape 20. Shape 21 is a desirable sensor shape if the X-ray cone beam is centered higher up above the chin to cover more efficiently the teeth region.

Figure 4:
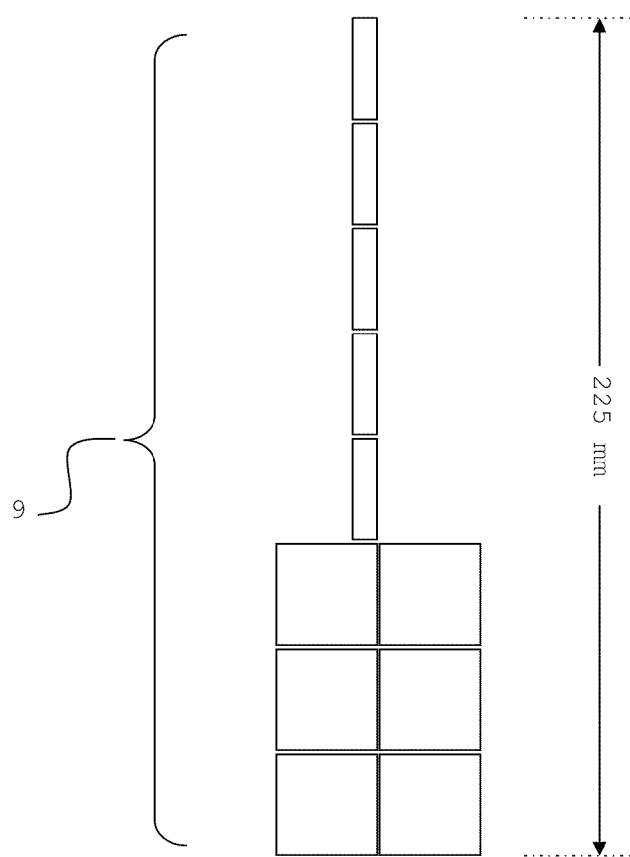
FIG. 4 illustrates a preferred shape of the active area of the invented X-ray sensor designed for dental extraoral X-ray imaging.

FIG. 4 shows another preferred shape 9 of the active area optimized not only for dental panoramic and tomographic imaging but also for cephalometric imaging. In cephalometric imaging an image of the complete human skull is acquired and, therefore, the vertical dimension of the slot part of the active sensor area has to be longer. Again, the shape of the active area shown in FIG. 4 is only an example and should be considered as one option of many possible to construct following the principles taught by the invention.

Figure 5:
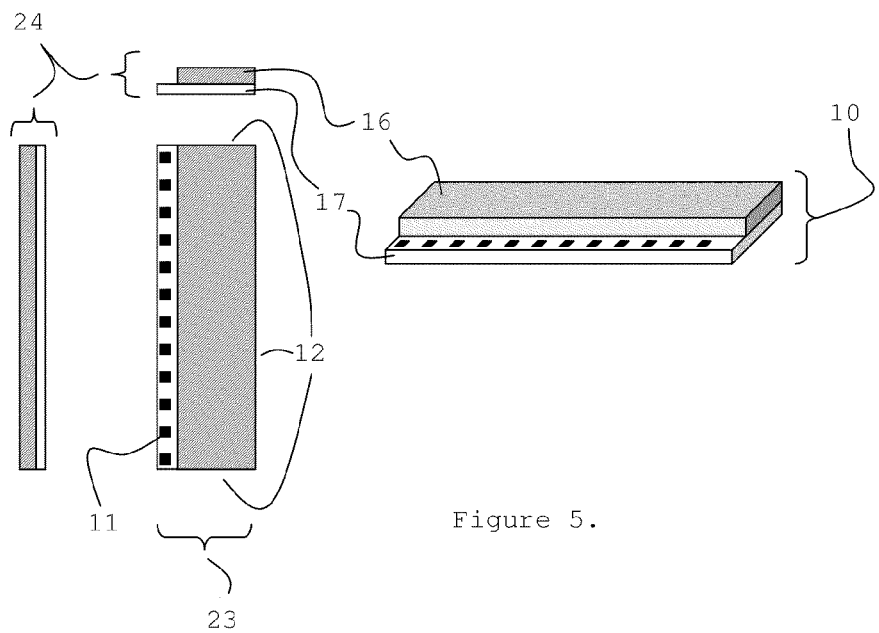
FIG. 5 illustrates plural views of one detector element.

FIG. 5 shows a drawing of one detector element 10 used to construct larger imaging areas. Top and side views 23 and 24, respectively, of the element 10 are shown. The structure of the element 10 reflects the structure of a CdTe-CMOS detector which comprises a CdTe crystal 16 connected to a CMOS readout circuit 17. The invention is, however, not limited to CdTe-CMOS technology. The element 10 has electrical connections 11 (typically ultrasonic wire bonds) at one side preventing side by side mounting of elements at this side. Other elements can be mounted very close or in physical contact to this one element 10 at all other sides 12.

The invention finds particular application with different kinds of tiled imaging devices comprising a scintillator or a phosphor on a CCD or CMOS sensor, or a combination os a CCD or CMOS imaging device(s) with a flat panel.

Figure 6:
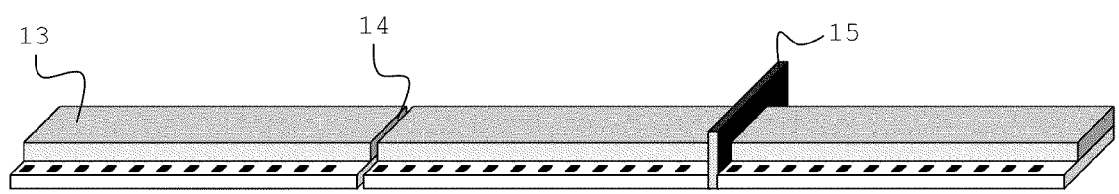
FIG. 6 illustrates a slot sensor with three separate detector elements.

FIG. 6 illustrates the invented manufacturing technique of mounting detector elements 13 side by side with a finite physical gap 14 between the elements 13. The gap 14 between the outside-most edges of the detector elements can be empty or it can be filled by placing an electrically isolating material 15 such as a mylar film between the elements 13. The width of the gap 14 is preferably in relation to the size of the detector pixel dimension and it can be smaller than the pixel size as long as electrical isolation is maintained and physical contact is avoided. This is important since the edges may be "rough" or diced with some acceptable degree of "chipping" and therefore the distance between the edges may be more appropriately be referred to as average distance. Therefore the gap 14 (average gap) should be a percentage of the detector pixel size. The width of the gap is preferably but not necessary a percentage function of the pixel size, i.e., 5% to 400% of the pixel size. A typical pixel size may be 0.1 mm. However, the invention also applies to pixels sized from 0.05 mm to 0.4 mm. For the 0.1 mm pixel, the gap advantageously is within the range of 0.005 mm to 0.4 mm, with 0.005 mm to 0.05 mm being the more advantageous, and 0.005 mm to 0.10 mm being most advantageous, since it offers adequate spacing but also a small enough gap compared to the pixel size.

The term "pixel" in the context of this invention usually has the meaning of the physical pixel size on the imaging device or on the detector. However, "pixel" also has the meaning and includes the final image pixel size as displayed in a viewing means. For example, the size of the final image pixel in the image as is displayed on a computer monitor.

In certain cases the user may choose to combine (or bin) the detector (or imaging device) physical pixels in order to be able to increase the x-ray photon statistics on the finally displayed image and/or to be able to process faster the resulting image. Thus, the image as displayed may have a final image pixel size that differs from the detector physical pixel size. For example the invention allows for a 2×2 binning, a 3×3 binning, etc. The displayed image may also have asymmetric binning, for example 1×2 or 2×1 etc.

For the purposes of this invention, reference to the width of the gap being preferably less than 400% of the pixel size, means that the physical pixel size of the detector or the final image pixel size of the final image as displayed, as the case might be. For example, if the detector pixel size is 0.1 mm and there is a 2×2 binning, then the final image as displayed will have a pixel size of 0.2×0.2 mm**2 and the gap between the individual detector elements should be less than 400% of the 0.2 mm, i.e., less than 0.8 mm. Thus, the gap between the detector elements is in relation to the pixel size as perceived by a viewer of the image and the higher the resolution of the final image, the smaller the gap should be.

In one embodiment, the inventive radiation imaging device is made of individual detectors Cd(Zn)Te detectors juxtaposed next to each other with an average physical gap of at least 0.005 mm between the edges of the Cd(Zn)Te detectors, a physical average gap of between 0.005 mm-0.4 mm between the edges being preferred. This gap can be provided by a film, e.g., by a mylar thick 0.005 mm-0.4 mm thick or alternatively by accurately placing the Cd(Zn)Te detectors using a microscope having an average gap in the above range.

Figure 7:
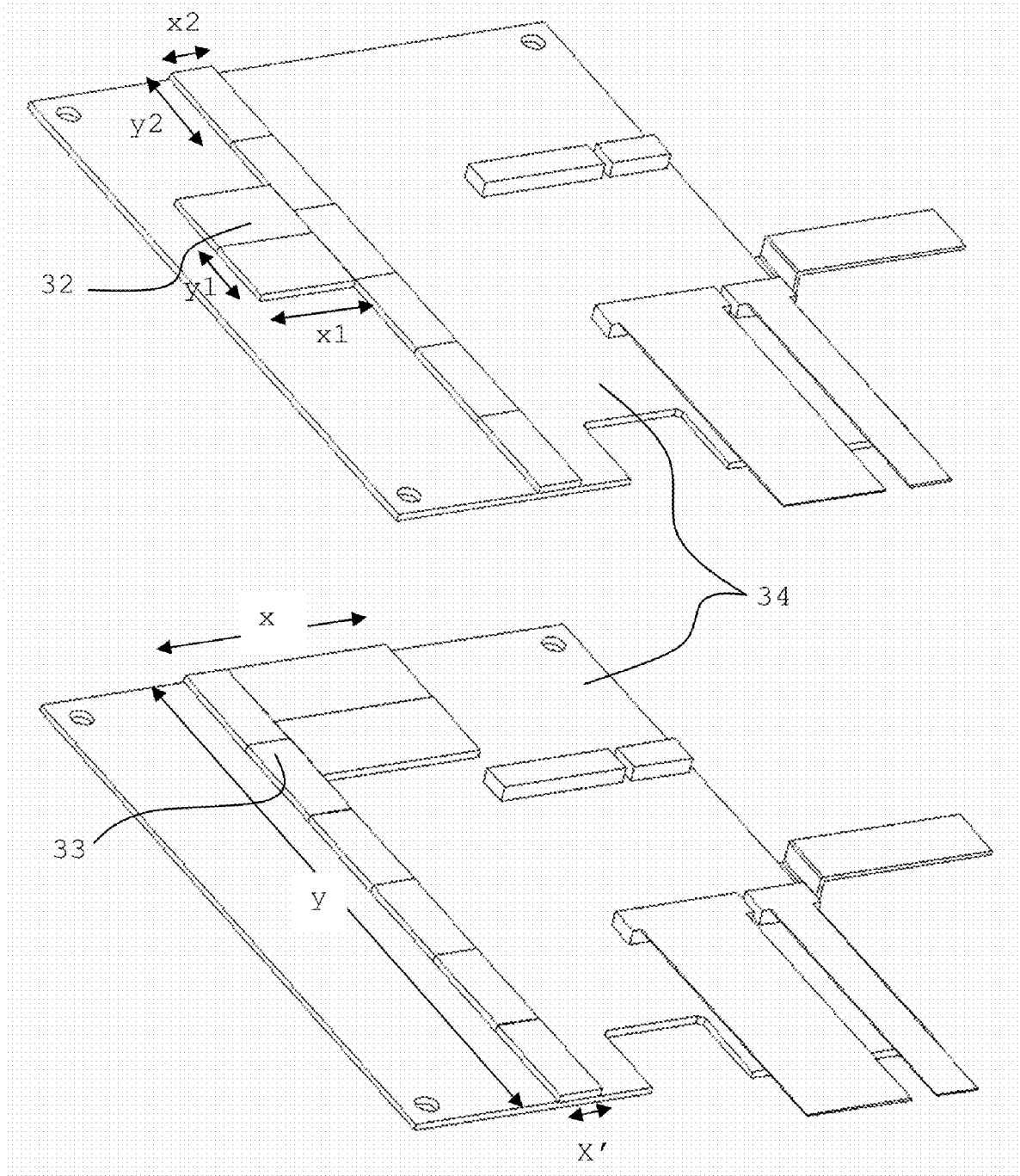
FIG. 7 illustrates two identical sensor substrates populated with detector elements to form different active sensor areas.

FIG. 7 shows how two different shapes 32 and 33 of active sensor area can be constructed on identical sensor substrates 34 (also referred to as detector module(s)). In this illustration the substrate/detector module 34 is a printed circuit board (PCB). The same substrate can accommodate a varying number of detector elements of different or identical shape and size to form a desired active sensor area. The benefit of this aspect of the invention is cost and time effective production.

FIG. 7 shows, for each of the identical sensor substrates/detector modules 34, a plurality of individual detectors defining an active area responsive to x-rays. The active areas each have a rectangular shape with an overall length y and an overall width x In each case the substrate/detector module 34 serves as a common motherboard with the active area comprises individual detectors of different rectangular shape commonly mounted on the mother board. As shown, a first of the detectors has a first active length y1 and a first active width x1, and a second of the two detectors has a second active length y2 and a second active width x2. As the two types of individual detectors have different rectangular shapes, at least one the first active length y1 and the second active length y2 are different or the first active width x1 and the second active width x2 are different. This allows the construction of the active area to be such that the active width x varies along the active length y (for example see active width x and x' in FIG. 7).

Figure 8:
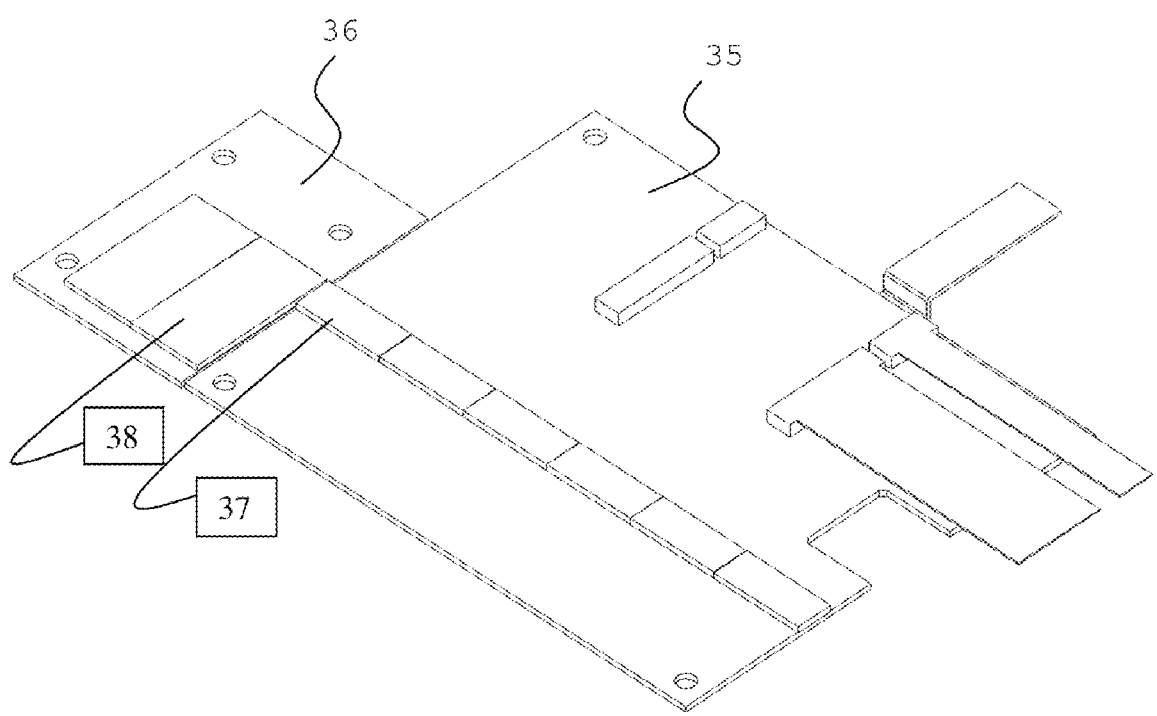
FIG. 8 illustrates a sensor constructed of two separate sensor substrates.

FIG. 8 shows how a desired sensor area can be constructed by combining two different sensor substrates 35 and 36 side by side in a detachable manner. In this example substrate 35 accommodates a slot like linear array sensor and substrate 36 accommodates a square shape sensor. The benefit of this aspect of the invention is as above effective production and product development. Using plural substrates allows the separate substrates to be used independently and flexibly in applications where an irregular shape of the sensor area is not required or in combination to form a shape of active area according to the present invention.

FIG. 8 shows a radiation imaging device comprised a first module 35 (i.e., first detector substrate) mounting a first individual detector 37 and a second module 36 (ie second detector substrate) detachable connected to the first module 35 and mounting a second individual detector 38. Together the first and second detectors define the active area responsive to x-rays. As shown, the first and second detectors are of different rectangular shape with at least one of their lengths and widths being different.

Figure 9:
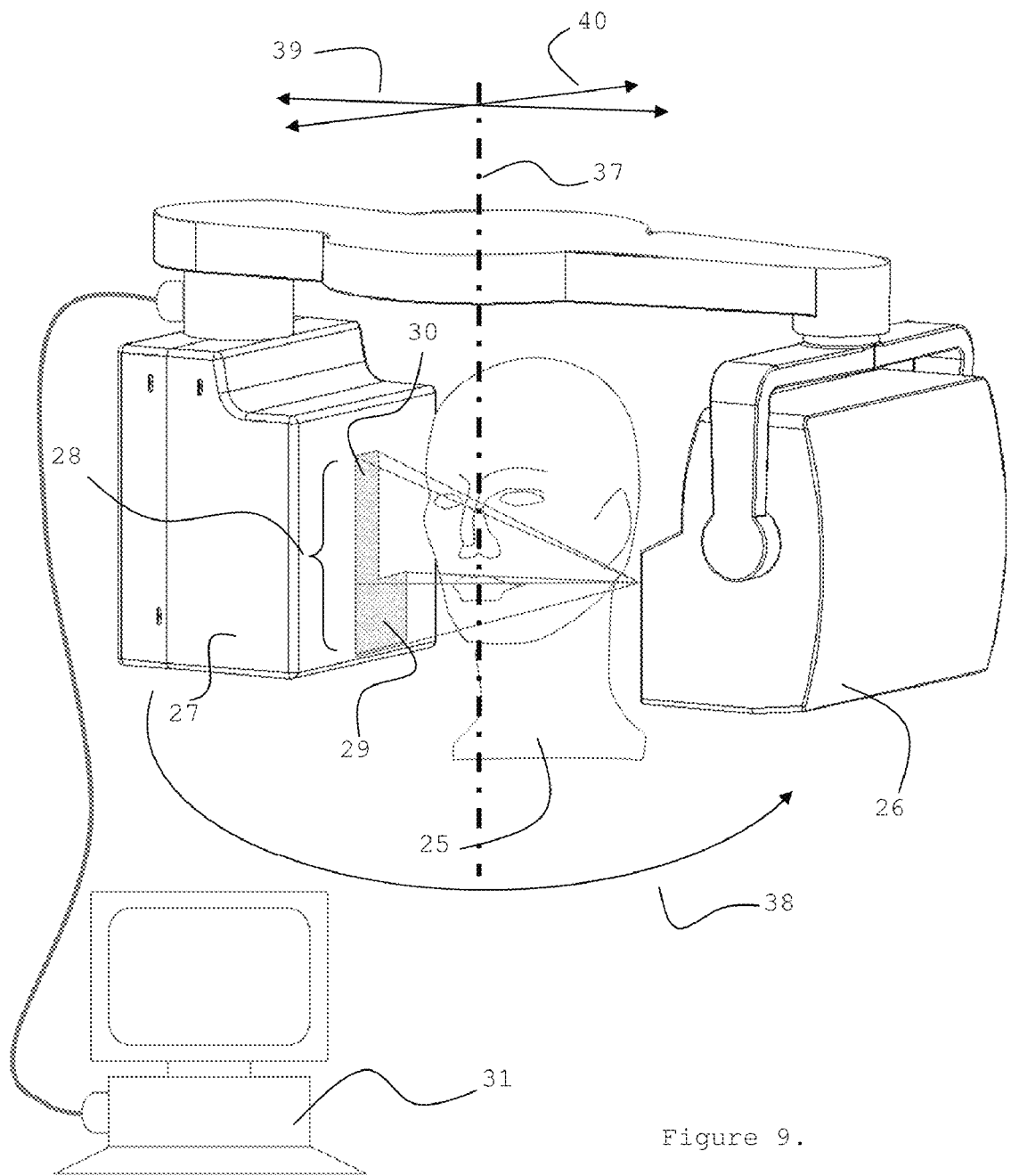
FIG. 9 is a schematic of a dental extra oral X-ray imaging system.

FIG. 9 illustrates the application of the invention to dental extra oral X-ray imaging. A patient 25 is placed between an X-ray source 26 and an X-ray imaging sensor 27 of a design according to the present invention. The image acquisition is performed as a rotational scan around the head of the patient. The X-ray beam shape 28 is in this illustration optimized for simultaneous acquisition of a panoramic image and a tomographic image. The tomographic image data is collected by the lower and wider part 29 of the sensor area while the narrower slot like full length 30 of the active area is used to collect the panoramic image data.

The data is acquired at a predefined rate as image frames each frame corresponding to a certain position of the X-ray source and sensor along the rotational path of the scan. The data is sent to a computer 31 for image reconstruction and display. A full panoramic layer or a local part of a panoramic layer as well as a transverse slice or a 3D image corresponding to a local part of a panoramic layer can be reconstructed from the data frames.

The system of FIG. 9 thus provides an extra-oral dental x-ray imaging system. The x-ray source 26 generates x-rays for exposure of such x-rays to the patient to be imaged. The inventive x-ray imaging devices 28, as disclosed above, are used for producing multiple frames during at least part of the exposure. At least one of the x-ray source and imaging device rotate around at least one rotational axis 37 defined by a spline 38, the axis being located between the x-ray source focal point and the x-ray imaging device and changing position along directions 39 and 40 during the scan.

Thus, the system provides an x-ray imaging device adapted for producing multiple frames from a single x-ray imaging device during at least part of the exposure. The x-ray imaging device comprises a plurality of individual semiconductor pixel detectors in an array defining an active area responsive to x-rays. The active area having a rectangular shape with length y and a width x, with the width x having at least two different values for corresponding ranges along the length y.

Each detector is composed of pixels. An average physical gap is defined between each set of adjacent edges of adjacent ones of the individual detectors, each of the average physical gaps of all of the plural individual detectors is up to 400% of a pixel size of the pixels of the image produced by the radiation imaging as displayed for viewing.

The computer 31, a processor, processes the frames of a single exposure to compose selectively at least two of a group of elements, the elements comprising (a) a predetermined dental panoramic layer image, (b) a local part of a non-predetermined dental panoramic layer image, (c) a transverse slice to a local part of a dental panoramic layer image; and (d) 3-D reconstruction of a volume corresponding to some local part of a dental panoramic layer.

Further, at least two preselected programs may be provided for exposure for executing corresponding exposure profiles to compose selectively at least two of a group of elements, the elements comprising (a) a panoramic image, (b) a cephalometric image, (c) a transverse slice to a local part of a dental panoramic layer image; and (d) a 3-D reconstruction of a volume of interest.

What is claimed is:

1. A radiation imaging device, comprising:
    a single imaging sensor comprised of a plurality of individual pixel detectors combined in an array defining an active area responsive to x-rays, each detector composed of pixels,
    said active area having an irregular rectangular shape with length y and a width x,
    the width x having at least two different values x and x' for corresponding ranges along the length y,
    an average physical gap is defined between each set of adjacent edges of closest adjacent ones of said individual detectors,
    each of said average physical gaps of all of said plural individual detectors is up to 400% of a pixel size of the pixels of the image produced by said radiation imaging as displayed for viewing.

2. The imaging device of claim 1, wherein the pixel size of the pixels of the image produced is a multiple of the physical pixel size of the individual pixel detectors, said detector pixels being binned to produce the produced image for display.

3. The radiation imaging device of claim 1, further comprising:
    a motherboard;
    said active area comprising two individual detectors of different rectangular shapes commonly mounted on the mother board,
    a first of the two detectors having a first active length y1 and a first active width x1, and
    a second of the two detectors having a second active length y2 and a second active width x2, wherein,
    at least one of i) the first active length y1 and the second active length y2, and ii) the first active width x1 and the second active width x2, are different.

4. The radiation imaging device of claim 1, further comprising:
    a first module mounting a first of two individual detectors;
    a second module detachable connected to the first module and mounting a second of two individual detectors, wherein,
    the first and second detectors define the active area responsive to x-rays,
    said first and second detectors are of different rectangular shapes,
    said first detector has a first active length y1 and a first active width x1,
    said second detector has a second active length y2 and a second active width x2, and
    at least one of i) the first active length y1 and the second active length y2, and ii) the first active width x1 and the second active width x2, are different.

5. The radiation imaging device of claim 1, further comprising:
    said active area comprising two individual detectors of different rectangular shapes,
    a first of the two detectors having a first active length y1 and a first active width x1, and
    a second of the two detectors having a second active length y2 and a second active width x2, wherein,
    the first active width x1 and the second active width x2 are different.

6. The radiation imaging device of claim 1, further comprising:
    a first module mounting a first of two individual detectors;
    a second module detachable connected to the first module and mounting a second of two individual detectors, wherein,
    the first and second detectors define the active area responsive to x-rays,
    said first and second detectors are of different rectangular shapes.

7. The radiation imaging device of claim 1, further comprising:
    at least one detector module commonly mounting said individual detectors, wherein,
    said individual detectors comprise at least two individual detectors juxtaposed next to each other with the average physical gap being 0.005 mm between the edges of the individual detectors.

8. The radiation imaging device according to claim 7, wherein,
    at least two individual detector modules of rectangular shape mount said individual detectors, and
    said individual detector modules are Cd(Zn)Te detectors mechanically arranged proximate to each other so as there the average physical gap is 0.005 mm between the edges of the Cd(Zn)Te detectors.

9. The radiation imaging device of claim 1, wherein, said active area is widest at a first distal end and narrowest at a second distal end.

10. The radiation imaging device of claim 1, wherein, said active area is narrowest at distal ends of the active area and widest in a center.

11. The radiation imaging device of claim 1, wherein, said active area is widest at distal ends of the active area and narrowest in a center.

12. The radiation imaging device of claim 1, wherein, said active area is symmetric.

13. The radiation imaging device of claim 1, wherein, said active area is asymmetric.

14. The radiation imaging device of claim 1, wherein, said active area is symmetric and includes an open space in a middle of the active area, a width and a length of said open space is each greater than said average physical gaps of the corresponding individual detectors surrounding said open space.

15. The radiation imaging device of claim 1, wherein, said active area includes an open space in a middle of the active area, a width and a length of said open space is each greater than said average physical gaps of the corresponding individual detectors surrounding said open space.

16. The radiation imaging device of claim 1, further comprising:
    a motherboard, the individual detectors mounted on the motherboard; and
    a film separating each of the individual detectors, the film from the motherboard between opposite edges of adjacent ones of the individual detectors.

17. The radiation imaging device of claim 15, wherein, said film is a mylar film.

18. The radiation imaging device of claim 17, wherein, said film is 0.005 mm thick, and
    said active area includes an open space in a middle of the active area, a width and a length of said open space is each greater than said average physical gaps of the corresponding individual detectors surrounding said open space.

19. A radiation imaging device, comprising:
    a single imaging sensor comprised of a plurality of individual pixel detectors positioned adjacently in an array defining an active area responsive to x-rays, each detector composed of pixels,
    each said individual detector having a rectangular shape and together defining an overall active area with a length y and a width x; and
    at least one detector module on which said individual detectors are mounted, wherein,
    said individual detectors comprise at least two individual detectors juxtaposed next to each other,
    an average physical gap is defined between each set of adjacent edges of adjacent ones of said individual detectors,
    each of said average physical gaps of all of said plural individual detectors is up to 400% of a pixel size of the pixels of the image produced by said radiation imaging as displayed for viewing.

20. An extra-oral dental x-ray imaging system, comprising:
    a. an x-ray source adapted for generating x-rays for exposure of such x-rays to an object to be imaged;
    b. an x-ray imaging device adapted for producing multiple frames from a single x-ray imaging device during at least part of the exposure, said x-ray imaging device comprising a plurality of individual semiconductor pixel detectors in an array defining an active area responsive to x-rays, each detector composed of pixels, said active area having a rectangular shape with length y and a width x, with the width x having at least two different values for corresponding ranges along the length y, an average physical gap is defined between each set of adjacent edges of adjacent ones of said individual detectors, each of said average physical gaps of all of said plural individual detectors is up to 400% of a pixel size of the pixels of the image produced by said radiation imaging as displayed for viewing;
    c. at least one rotational axis around which at least one of the x-ray source and imaging device rotates along a spline, the axis being located between the x-ray source focal point and the x-ray imaging device; and
    at least two preselected programs for exposure for executing corresponding exposure profiles to compose selectively at least two of a group of elements, the elements comprising
    (a) a panoramic image,
    (b) a cephalometric image,
    (c) a transverse slice to a local part of a dental panoramic layer image; and
    (d) a 3-D reconstruction of a volume of interest.

* * * * *